United States Patent [19]

Hyde

[11] Patent Number: 4,655,743

[45] Date of Patent: Apr. 7, 1987

[54] FROG ASPIRATOR

[76] Inventor: Lawrence L. Hyde, 2900 Baltimore, Suite 650, Kansas City, Mo. 64108

[21] Appl. No.: 730,803

[22] Filed: May 6, 1985

[51] Int. Cl.[4] ............................................. A61B 17/32
[52] U.S. Cl. ........................................ 604/22; 128/305
[58] Field of Search ...................... 128/305, 751-753, 128/305.1, 310, 304; 604/22

[56] References Cited

U.S. PATENT DOCUMENTS

| | | | |
|---|---|---|---|
| 1,867,624 | 7/1932 | Hoffman | 128/305 X |
| 3,815,604 | 6/1974 | O'Malley et al. | 128/305 X |
| 3,902,498 | 9/1975 | Niederer | 128/305 |
| 4,011,869 | 3/1977 | Seiler | 128/305 X |
| 4,425,115 | 1/1984 | Wuchinich | 604/22 |

OTHER PUBLICATIONS

Brochure "The McIntyre Cannula" by D. J. McIntyre, apparent publication date Apr. 1976.
Storz Product Catalog, "Ophthalmic Products", 18th Ed. published 1983, pp. 22-27.
"Extracapsular Cataract Surgery" by Jared M. Emery and David J. McIntyre, published by C. V. Mosby Co. 1983, pp. 205-215 and 164-166.
"Cataract Surgery and Its Complications" by Norman S. Jaffe, 4th Ed., C. V. Mosby Co. pub. 1984, pp. 246-255 and 263-265.

Primary Examiner—Michael H. Thaler
Attorney, Agent, or Firm—Litman, Day & McMahon

[57] ABSTRACT

An irrigation-aspiration device includes an outer cannula and an inner cannula reciprocatable within the outer cannula. Irrigating fluid is flowable between the inner and outer cannula. The inner cannula is bent along the length thereof and springy so as to be biased near an outer end thereof against one side of the outer cannula. A port opens into the inner cannula and is positioned so as to selectively abrade against an operable end of the outer cannula with a biting or cutting action. An inner lumen of the inner cannula is connected to a vacuum or suction source such that during surgery fragments of the eye may be drawn into the port of the inner cannula and cut by abrasion against the end of the outer cannula and thereafter pulled through the inner cannula and away from the eye. This cutting action may be utilized to remove attached fragments of the anterior capsule, pieces of vitreous, nuclear and cortex material, and to biopsy the iris.

3 Claims, 8 Drawing Figures

FROG ASPIRATOR

BACKGROUND OF THE INVENTION

The present invention relates to surgical instruments for use in ophthalmic surgery and, in particular, to aspiration-irrigation devices utilized for cataract surgery.

During cataract surgery, various parts of the eye, including the lens, are removed and/or the clouded lens is ultrasonically pulverized and then removed. Many techniques have been conventionally utilized to remove various parts of the eye in conjunction with the lens. For example, a conventional aspiration-irrigation device has been used for a number of years in both planned extracapsular surgery and for cortical cleanup after Phachoemulsification techniques. Such devices often include an inner and outer cannula cooperating with a source of irrigating fluid and with a vacuum or suction developing source. The inner cannula reciprocates within the outer cannula and includes a port on the end which is connected through an inner lumen with the vacuum source.

Irrigating fluid is allowed to flow between the inner and outer cannulas so as to irrigate the eye during utilization of the device. In various devices, the irrigating fluid may flow through and out the end of the outer cannula or may flow through ports in the sides of the outer cannula. The vacuum is selectively controlled by the surgeon to allow only the material which is desired to be removed to be withdrawn from the eye. The conventional aspiration-irrigation devices have been frequently used to remove cortical material from the posterior capsule. In general, the cortical material is drawn into the port of the interior cannula and a vacuum is applied to hold it there. The device is then maneuvered such that the cortical material is pulled away from the posterior capsule without tearing or rupturing the capsule, and the material is pulled into the interior cannula to be drawn therethrough by suction selectively applied by the surgeon.

Such techniques are somewhat effective on the cortical material which is easily drawn into the port of the inner cannula and thereafter through the inner cannula by the selectively applied suction. However, there are often fragments of other parts of the eye which should be removed during the surgery, but which are not as easily loosened from the eye as is the cortical material. For example, a piece or tag of the anterior capsule may remain after a standard serration cutting, sometimes referred to as "beer can opener", cutting and removal of the anterior capsule. In the past, one process, referred to as the Kelman "toilet-tissue" technique, has been utilized for removing such a tag. In this technique, the tag is grasped by intraocular irrigating forceps and briskly snapped. This technique often adequately removes the tag, but in some situations the zonules are broken.

Another technique used for removing anterior capsule fragments has been to utilize an aspiration-irrigation device in conjunction with a Franceschetti hook. In this technique, the fragment is sucked against the port on the interior cannula, while the hook is inserted into the port so as to firmly grasp the fragment. The hook, while still in the port, is then pulled radially inward toward the central axis of the eye to tear the fragment. This technique can produce unintended tearing and does not cleanly remove the anterior capsule fragments.

It is often desirable during eye surgery to remove various fragments or filaments from within the eye which are attached to some other structure and are not easily removed by tugging or tearing, without damaging the structure to which it is attached or a surrounding structure.

OBJECTS OF THE INVENTION

Therefore, the objects of the present invention are: to provide an aspiration-irrigation device which allows a surgeon to cut fragments or filaments from surrounding tissue, while providing aspiration-irrigation structure compatible with conventional uses of aspiration-irrigation devices; to provide such a device which allows cutting action to occur at the suction port of the inner cannula, such that cut fragments may be easily withdrawn by means of suction applied to an inner lumen of the inner cannula; to provide such a device which allows the surgeon to easily modify the size of the port of the inner cannula by reciprocating movement between the inner and outer cannulas, such that the size of the material to be drawn into the port can be varied; to provide a method for utilization of such a device which allows selective removal of various attached fragments and filaments from within the eye during surgery in such a manner as to prevent damage to surrounding tissue; and to provide such a device which is relatively easy to manufacture, simple to use and well suited for the intended usage thereof.

Other objects and advantages of this invention will become apparent from the following description taken in conjunction with the accompanying drawings wherein are set forth, by way of illustration and example, certain embodiments of this invention.

SUMMARY OF THE INVENTION

An aspiration-irrigation device is provided which comprises an outer cannula, an inner cannula, a suction or vacuum source and an irrigating fluid source. The inner cannula is slidably positioned within the outer cannula so as to be selectively and generally axially reciprocal therein by means of a surgeon moving a manipulative end of one cannula (or the structure attached thereto) with respect to the other. The inner cannula includes an aperture or port near an operative end thereof which communicates with an internal lumen thereof which in turn flow communicates with the vacuum source. The suction source is selectively appliable by a surgeon so as to draw fluid and/or solid materials into the port and through the lumen. The operative end of the internal cannula is selectively extendable beyond an operative end of the outer cannula such that the port extends beyond the outer cannula. The inner cannula is preferably bent so as to form a V-shape at an intermediate location therealong and is springy so as to urge the operative end of the inner cannula toward one side of the outer cannula and the inner cannula at the location whereat same is bent against a diametrically opposite side of the outer cannula. In particular, the V-shape of the inner cannula must be compressed to place the inner cannula in the lumen of the outer cannula. The port is positioned so as to abrade against the operative end of the outer cannula when the inner cannula is moved therepast, that is, when the port is radially positioned inward of the operative end. The V-shape of the inner cannula in cooperation with the springy or resilient nature thereof urges the port, especially the outer lip of the port against the end of the outer cannula as it abrades therepast. The suction mechanism may comprise a vacuum pump with suitable connecting hose such as is found on Phacoemulsificers, an aspirator squeeze bulb, a syringe type device, or the like.

The fluid source is in flow communication with the device such that the irrigation fluid is allowed to flow between the inner and outer cannulas and to flow into an eye near the operative end of the outer cannula during surgery. The irrigant fluid source may include a positive pressure pumping mechanism, a gravity feed fluid system, or the like. The fluid source may be continuous at a fixed rate or be variably controlled by the surgeon. Sealing means are provided near the manipulative ends of the inner and outer cannulas to prevent the irrigant fluid from flowing therebetween. Sizes of the inner and outer cannulas, as well as the port, may be varied in accordance with the invention; however, a device having a twenty gauge inner cannula and a seventeen gauge thin wall outer cannula with a 0.5 millimeter port has been found to be quite satisfactory. Conventional inner cannulas having ports of 0.2, 0.3, and 0.7 millimeters are commercially available and it is foreseen that inner cannulas for the present invention having ports of various sizes may perform satisfactorily for some utilizations.

Preferably, the operative end of the outer cannula is relatively blunt, as opposed to very sharp, so as to prevent accidental injury to structures within the eye which are not intended to be removed. In use, the inner cannula is slid or reciprocated axially relative to the outer cannula by the surgeon to a position where a fragment to be removed is near or touching the port. Suction is applied to the port through the suction mechanism so that the fragment is drawn partially into the port. The inner cannula is then moved relative to the outer cannula so that the outer lip of the port abrades past the operative end of the outer cannula thereby pinching the fragment intermediately and gnawing or cutting the fragment loose, thereby allowing the cut fragment to be drawn into the port and then the lumen of the inner cannula. Although a sharp cutting edge could be utilized for the purpose, a relatively dull end, especially a lip, on the outer cannula and a similar wall or lip on the port will produce an abrading action that normally functions quite satisfactorily.

The drawings constitute a part of this specification and include exemplary embodiments of the present invention and illustrate various objects and features thereof.

It is noted that certain dimensions within the drawings have been exaggerated in certain of the figures in order to better emphasize the features thereof.

DETAILED DESCRIPTION OF THE INVENTION

As required, detailed embodiments of the present invention are disclosed herein; however, it is to be understood that the disclosed embodiments are merely exemplary of the invention which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

Figure 1:
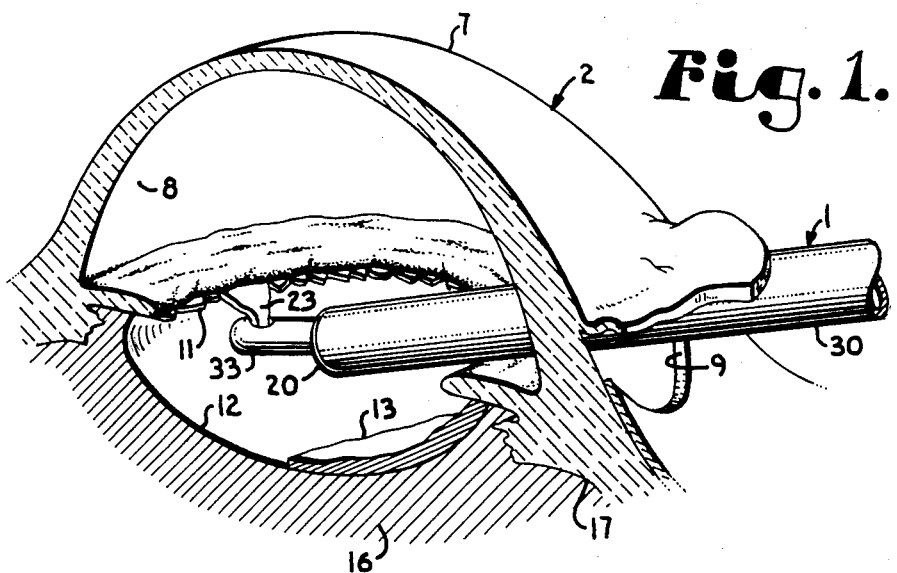
FIG. 1 is a fragmentary and perspective view of an eye having a surgical procedure performed thereon by an aspiration-irrigation device according to the present invention.
Figure 2:
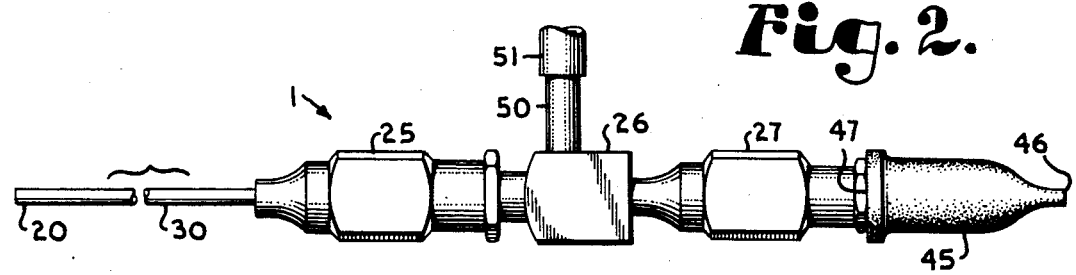
FIG. 2 is a fragmentary and enlarged top plan view of the aspiration-irrigation device.
Figure 3:
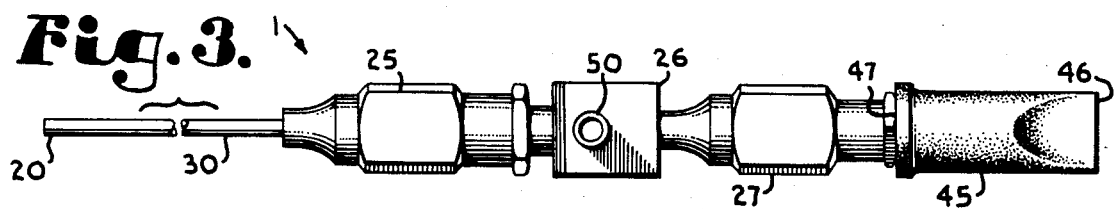
FIG. 3 is a fragmentary and enlarged side elevational view of the aspiration-irrigation device.
Figure 4:
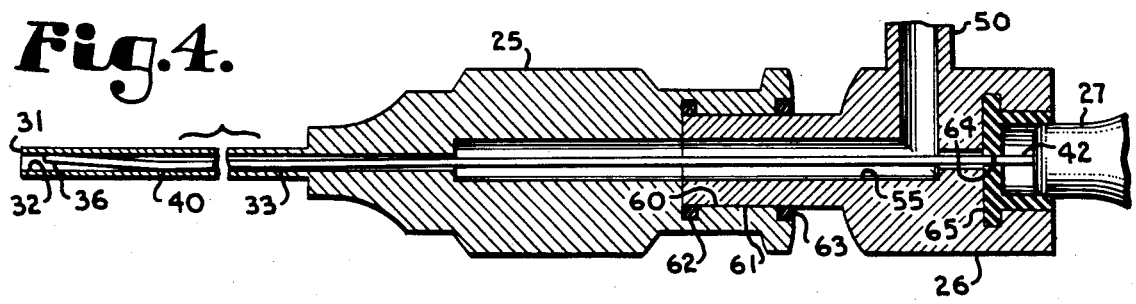
FIG. 4 is a further enlarged, cross-sectional view of the aspiration-irrigation device, taken along line 4—4 of FIG. 2.
Figure 5:
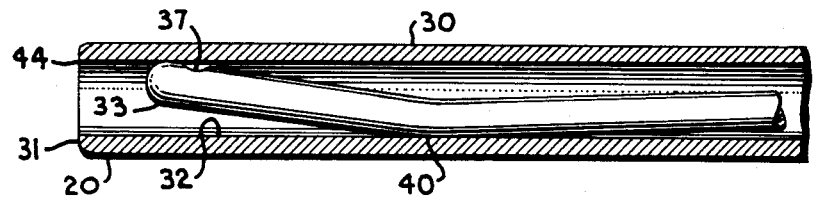
FIG. 5 is a still further enlarged and fragmentary cross-sectional view of an operative end of the aspiration-irrigation device showing an inner cannula in an inner position relative to an outer cannula.
Figure 6:
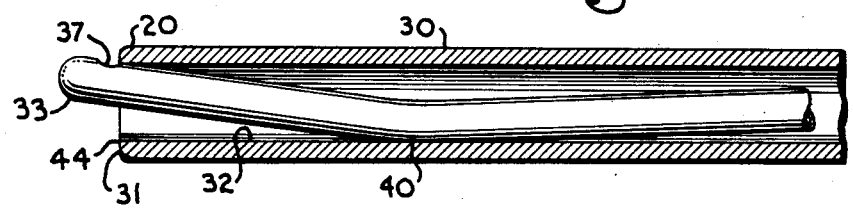
FIG. 6 is a fragmentary and enlarged cross-sectional view of the aspiration-irrigation device similar to FIG. 5, but showing a port of the inner cannula extended relative to the outer cannula.

The reference numeral 1 generally represents a aspiration-irrigation device according to the present invention. As seen in FIG. 1, the device 1 is utilized in conjunction with surgical procedures on a human eye 2 upon which cataract surgery or the like is being performed.

The eye 2, as shown in FIG. 1, includes a cornea 7 arched above an interior chamber 8. The clouded portion of the eye forming a cataract, that is the hardened lens, has previously been removed through a surgical opening 9 by one of several techniques for removing such cataracts. An anterior capsule for the lens has also previously been removed by a serration cutting technique and peripheral triangular fragments 11 of the anterior capsule remain attached to the eye 2 and are located spaced radially from the central eye axis. A posterior capsule 12 remains intact with a partial cortex or cortical layer 13 positioned thereon. Vitreous humor material 16 is positioned beneath the posterior capsule 12 and generally fills the eyeball posterior cavity 17.

Figure 7:
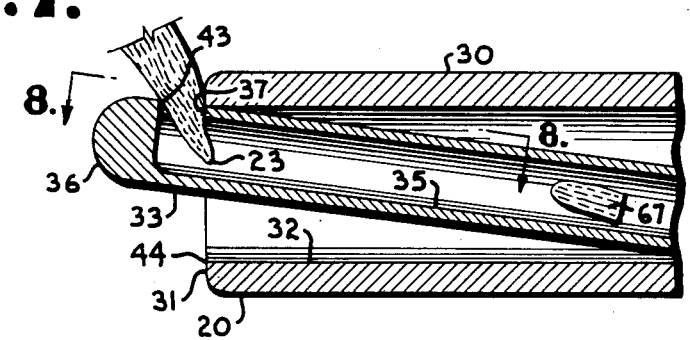
FIG. 7 is a still further enlarged and fragmentary cross-sectional view of the aspiration-irrigation device similar to FIG. 5 wherein the port is shown with an eye fragment therein and abrading against an operative end of the outer cannula.
Figure 8:
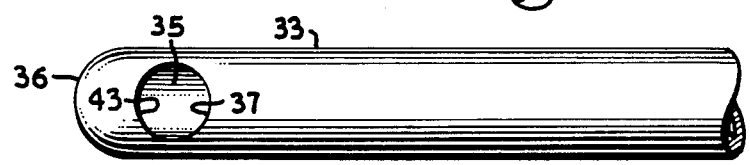
FIG. 8 is a side elevational view of the inner cannula taken along line 8—8 of FIG. 7.

The aspiration-irrigation device 1 is positioned through the surgical opening 9 such that an operative end 20 is located within the interior chamber 8 of the eye 2. A remaining and undesirable large fragment 23 of the anterior capsule fragments 11 is positioned near the device operative end 20. The fragment 23 is also shown in FIG. 7.

The aspiration-irrigation device, as seen in FIGS. 2 through 8, comprises a first section 25, a second section 26 and a third section 27. An outer cannula 30 is mounted on the first section 25 and extends generally axially thereinto. The outer cannula 30 has an operative end 31 and an inner lumen 32.

An inner cannula 33 is axially mounted on the third section 27. The inner cannula 33 is somewhat smaller in diameter than the outer cannula interior lumen 32 and is operably slidably and snugly received therein such that the inner cannula 33 is somewhat compressed and biased against diametrically opposed sides of the outer cannula lumen 32. The inner cannula 33 has an internal lumen 35 and a tip or operative end 36. The inner cannula also has an aperture or port 37 radially extending through a side thereof and communicating with the lumen 35. In the illustrated embodiment, the port 37 is approximately 0.5 mm. in diameter, although ports of other sizes may be utilized within the invention. The inner cannula 33 is springedly bent in a V configuration at location 40 such that the inner cannula 33 is urged or biased against the exterior cannula lumen 32 at both the bend location 40 and near the operative end 36. The inner cannula 33 is of such a length that it may be selectively reciprocated within the outer cannula 30 by manipulation of the device third section 27 and consequent manipulation of an inner cannular manipulative end 42, so as to extend substantially from the outer cannula operative end 31 or alternatively be completely received within the outer cannula 30. The outer cannula 30 is manipulated by grasping the device first section 25 and/or the second section 26. The inner cannula 33 is also sufficiently long that the port 37 may be extended beyond the outer cannula operative end 31. The port 37 is also positioned so as to cooperate with the outer cannula operative end 31, such that when the inner cannula 33 is reciprocated with respect to the outer cannula 30, a lip 43 of the port 37 may be selectively abraded against a lip 44 of the outer cannula operative end 31.

The device 1 also includes a suction means, such as a frog aspirator 45. A suitable aspirator of this type is sold by Storz. The aspirator 45 operably functions by a surgeon depressing or alternatively releasing the sides of the aspirator 45. When the sides of the aspirator 45 are squeezed, material is expelled from a discharge end 46 thereof. When the sides of the aspirator 45 are released an internal suction is produced at a suction end 47 opposite the discharge 46. The suction end 47 of the aspirator 45 is operably flow connected to the inner cannula lumen 35 such that, when pressure is released from the aspirator 45, a suction is created within the lumen 35. The lumen 35 flow communicates with the interior of the aspirator 45 in a conventional manner so as to allow generally unrestricted flow from the port 37 through the lumen 35 and into the aspirator 45, when suction is produced therein. It is foreseen that other suction means such as a vacuum pump or a syringe could be utilized for the same purpose; however, an aspirator of the type shown has been found to provide very efficient control of the suction within the inner cannula 33 by the surgeon.

The second section 26 of the device 1 includes an irrigant fluid port 50 extending radially outward therefrom. The port 50 is adapted to mate with a suitable and conventional partly shown irrigant hose and reservoir 51. The irrigant port 50 communicates with a channel 55 passing through the second section 26 and coaxially mating with the outer cannula lumen 32 such that irrigant fluid is free to flow from an irrigant source to the device 1 and out the outer cannula operative end 31. The second section 26 slidably mates with the first section 25 by means of respective coaxial sliding connectors 60 and 61 which may be luer lock type connectors and which are sealed by suitable sealing means such as O-rings 62 and 63. The third section 27 slides axially with respect to the first section 25 and the second section 26, as the inner cannula 33 slides within the outer cannula lumen 32. The inner cannula 33 slides within an aperture 64 of a suitable sealing disc 65 which seals about the inner cannula 33 to prevent flow of the irrigant fluid in a direction other than toward the operative end 20 of the device 1.

In use, the aspiration-irrigation device 1 is injected through a surgical opening 9 in the eye 2 and may be used in a conventional manner to vacuum debris from various ophthalmic procedures or the device 1 may be also utilized to remove the cortex 13 by conventional methods. Additionally, because of the structure disclosed herein, the device 1 may also be advantageously utilized to remove flaps or strands of tissue which are connected to various structures in the eye 2 in such a manner that avoids simply pulling the flap or strand from the eye which may cause damage to the surrounding tissue or result in other complications. For this purpose, the device 1 is positioned such that the port 37 is closely adjacent to or touching the tissue to be removed. For purposes of illustration, it is assumed in FIGS. 1 and 7 that the flap 23 is to be removed. The port 37 is positioned adjacent to the flap 37 and a vacuum or suction is produced within the inner cannula lumen 35 by operation of the aspirator 45 by the surgeon. The suction draws a portion of the flap 23 into the port 37, as shown in FIG. 7. The surgeon then manipulates the inner cannula 33 so as to reciprocate or generally axially slide within the outer cannula 30, such that the port 37 and consequently the portion of the flap 23 within the port 37 abrades against the outer cannula operative end 31. In particular, the flap 23 is pinched between the outer cannula end lip 44 and the port lip 43. Continued pressure is applied to the inner cannula 33 relative to the outer cannula 30 until the inner cannula tip 36 is drawn into the outer cannula lumen 32 and a piece of the flap 23 is completely severed from the eye 2. The operative end 31 of the outer cannula 30 is preferably relatively blunt so as to preclude injury to tissue which is not to be removed. It has been found that the abrading action of the port 37 against the outer lumen end 31 provides sufficient cutting to remove pieces of capsule, vitreous, cortex or even to biopsy the iris. The port 37 may be operably made smaller, if the surgeon requires a smaller opening for a fragment, by simply positioning the port 37 so as to be partially occluded by the end of the outer cannula 30. Although positions of eye structures such as the posterior capsule or iris may be removed in accordance with the methods described herein, when special requirements, such as biopsy, require removal thereof, in normal cataract surgery, the surgeon is very careful not to pull structures such as the iris or posterior capsule into the port 37. After a piece, such as flap segment 67 as is seen in FIG. 7, is cut from the structure to be removed the cut piece 67 is drawn through the lumen 35 by the aspirator 45 and into the aspirator 45, after which it may be expelled from the discharge end 46 thereof. The inner cannula 33 is then extended from the outer cannula 30 and this process is repeated as often as necessary to completely disengage all of the structure to be removed.

The piece 67 will often be drawn completely through the lumen 35 before repeating the operation on the flap 23; however, for purposes of illustration, both the piece 67 and flap 23 are simultaneously shown in the inner cannula 33 in FIG. 7.

It is to be understood that while certain forms of the present invention have been illustrated and described herein, it is not to be limited to the specific forms or arrangement of parts described and shown.

What is claimed and desired to be secured by Letters Patent is as follows:

1. An ophthalmic aspiration-irrigation device for use in surgery comprising:
   (a) an outer cannula having an internal lumen and a tip at an operative end thereof; said outer cannula tip having an aerture therethrough;
   (b) an inner cannula operably positioned within said outer cannula lumen and having an operative end and an internal lumen; said inner cannula being generally axially slidable relative to said outer cannula; said inner cannula being substantially smaller in diameter than an interior of said outer cannula entirely therealong so as to form a channel therebetween; said channel being flow connected to said aperture at said outer cannula tip;
   (c) said inner cannula also having a port operably positionable during sliding of said inner cannula with respect to said outer cannula such that said port abrades against said outer cannula operative end;
   (d) irrigation means communicating with said channel such that fluid irrigant may be selectively passed through said channel and out said aperture at said outer cannular tip: and
   (e) suction means operably cooperating with said inner cannula lumen and being manipulative so as to selectively provide suction to said inner cannula port through said inner cannula lumen.

2. The device according to claim 1 wherein:
   (a) said outer cannula operative end is relatively blunt whereat said outer cannula operative end abrades against a lip of said port.

3. An ophthalmic aspiration-irrigation device for use in surgery comprising:
   (a) an outer cannula having an internal lumen and an operative edd with a tip and an aperture at said operative end;
   (b) an inner cannula operably positioned within said outer cannula and having an operative end and an internal lumen; said inner cannula being selectively manipulative so as to slide axially relative to said outer cannula; said inner cannula aperture a substantially smaller diameter than said outer cannula aperture and said inner cannula and outer cannula forming a channel therebetween; said channel flow communicating with said tip;
   (c) said inner cannula having a port operably positionable during sliding of said inner cannula with respect to said outer cannula such that an outer lip of said port abrades against an inner lip of said outer cannula operative end;
   (d) a biasing bend intermediate along said inner cannula for urging said inner cannula port lip against said outer cannula operative end lip during manipulative operation of said device; said inner cannula being springy and compressed when positioned within said outer cannula such that said port lip and said inner cannula bend are urged toward diametrically opposed sides of said outer cannula lumen such that said port lip is urged against said outer cannula operative end lip as said lips abrade;
   (e) irrigation means communicating with said channel for selectively providing fluid irrigant through said aperture to said tip; and
   (f) suction means operably cooperating with said inner cannula lumen and being manipulative so as to selectively provide suction to said inner cannula port through said inner cannula lumen.

* * * * *